US006673597B2

(12) United States Patent
Wolf et al.

(10) Patent No.: US 6,673,597 B2
(45) Date of Patent: Jan. 6, 2004

(54) GROWTH STIMULATION OF BIOLOGICAL CELLS AND TISSUE BY ELECTROMAGNETIC FIELDS AND USES THEREOF

(75) Inventors: David A. Wolf, Houston, TX (US); Thomas J. Goodwin, Friendswood, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/798,854

(22) Filed: Feb. 28, 2001

(65) Prior Publication Data

US 2002/0009797 A1 Jan. 24, 2002

Related U.S. Application Data

(62) Division of application No. 09/587,028, filed on Jun. 2, 2000, now Pat. No. 6,485,963.

(51) Int. Cl.[7] ................................................ C12M 1/10
(52) U.S. Cl. ................................. 435/298.2; 435/299.1
(58) Field of Search ........................... 435/173.1, 173.8, 435/298.2, 299.1

(56) References Cited

U.S. PATENT DOCUMENTS

| | | | | | |
|---|---|---|---|---|---|
| 2,996,429 | A | * | 8/1961 | Toulmin, Jr. ................ | 435/391 |
| 3,133,003 | A | * | 5/1964 | Schaefer et al. ........ | 435/173.8 |
| 3,871,961 | A | * | 3/1975 | Gianessi .................. | 435/173.8 |
| 4,377,639 | A | * | 3/1983 | Lee ......................... | 435/299.1 |
| 4,487,834 | A | * | 12/1984 | Brighton .................... | 435/173 |
| 4,703,010 | A | * | 10/1987 | Yunker et al. ........... | 435/173.8 |
| 4,762,795 | A | * | 8/1988 | Masson .................... | 435/173.8 |
| 4,939,151 | A | * | 7/1990 | Bacehowski et al. ........ | 435/402 |
| 5,134,070 | A | * | 7/1992 | Casnig ..................... | 435/173.6 |
| 5,270,205 | A | * | 12/1993 | Rogalsky ................. | 435/298.1 |
| 5,316,945 | A | * | 5/1994 | Minuth .................... | 435/297.3 |
| 5,344,454 | A | * | 9/1994 | Clarke et al. ............. | 623/23.72 |
| 5,919,679 | A | * | 7/1999 | Blackman et al. ........ | 435/173.1 |
| 6,022,733 | A | * | 2/2000 | Tam et al. ................ | 435/287.1 |
| 6,066,495 | A | * | 5/2000 | Fofonoff et al. .......... | 435/289.1 |

* cited by examiner

Primary Examiner—David A. Redding
(74) Attorney, Agent, or Firm—James M. Cate

(57) ABSTRACT

The present invention provides systems for growing two or three dimensional mammalian cells within a culture medium facilitated by an electromagnetic field, and preferably, a time varying electromagnetic field. The cells and culture medium are contained within a fixed or rotating culture vessel, and the electromagnetic field is emitted from at least one electrode. In one embodiment, the electrode is spaced from the vessel. The invention further provides methods to promote neural tissue regeneration by means of culturing the neural cells in the claimed system. In one embodiment, neuronal cells are grown within longitudinally extending tissue strands extending axially along and within electrodes comprising electrically conductive channels or guides through which a time varying electrical current is conducted, the conductive channels being positioned within a culture medium.

25 Claims, 11 Drawing Sheets

GROWTH STIMULATION OF BIOLOGICAL CELLS AND TISSUE BY ELECTROMAGNETIC FIELDS AND USES THEREOF

This application is a division of application Ser. No. 09/587,028, filed Jun. 2, 2000 now U.S. Pat. No. 6,485,963.

ORIGIN OF THE INVENTION

The invention described herein was made by an employee of the United States Government and may be manufactured and used by or for the Government of the United States of America for governmental purposes without the payment of any royalties thereon or therefor.

BACKGROUND OF THE INVENTION

1. Field of the Invention

The present invention relates generally to the fields of biophysics, tissue regeneration, tissue culture, and neurobiology. More specifically, the present invention relates to the use of an electromagnetic field, and preferably, a time varying electromagnetic field, for potentiation of or controlling the growth of biological cells and tissue, such as mammalian tissue. More specifically, the present invention relates to the use of an electromagnetic field for controlling the growth of neural cells and tissues. The preferred embodiment utilizes two-dimensional conducting plate electrodes and may be applied to conventional, two dimensional tissue cultures or to three-dimensional cultures. Three dimensional cultures may be achieved in actual microgravity or by rotating wall vessel technology which simulates the physical conditions of microgravity, and in other, conventional three-dimensional matrix based cultures. The electromagnetic field, preferably a time varying electromagnetic field, is achieved in the vicinity of the electrode by passing, through the electrode, a time varying current.

2. Description of the Related Art

Growth of a variety of both normal and neoplastic mammalian tissues in both mono-culture and co-culture has been established in both batch-fed and perfused rotating wall vessels (1–2), and in conventional plate or flask based culture systems. In some applications, growth of three-dimensional structure, e.g., tissues, in these culture systems has been facilitated by support of a solid matrix in the form of biocompatible polymers and microcarriers. In the case of spheroidal growth, three-dimensional structure has been achieved without matrix support (3–6). NASA rotating wall tissue culture technologies have extended this three dimensional capacity for a number of tissues and has allowed the tissue to express different genes and biomolecules. Neuronal tissue has been largely refractory, in terms of controlled growth induction and three dimensional organization, under conventional culture conditions. Actual microgravity, and to a lesser extent, rotationally simulated microgravity, have permitted some enhanced nerve growth (Lelkes et al). Attempts to electrically stimulate growth have utilized static electric fields, static magnetic fields, and the direct passage of current through the culture medium, though not the induction of a time varying electromagnetic field in the culture region.

Neuronal tissue comprises elongated nerve cells composed of elongated axons, dendrites, and nuclear areas. Axons and dendrites are chiefly responsible for transmission of neural signals over distance and longitudinal cell orientation is critical for proper tissue formation and function. The nucleus plays the typical role of directing nucleic acid synthesis for the control of cellular metabolic function, including growth. In vivo, the neuronal tissue is invariably spatially associated with a system of feeder, or glial, cells. This three dimensional spatial arrangement has not been reproduced by conventional in vitro culture. Investigators, Borgens R B et al, and others, have utilized static electric fields in an attempt to enhance nerve growth in culture. (Valentini et al) with some success to either alter embryonic development or achieve isolated nerve axon directional growth. However, actual potentiation of growth or genetic activity causing such, have not been achieved. Mechanical devices intended to help grow and orient three dimensional mammalian neuronal tissue are currently available. Fukuda et al. (7) used zones formed between stainless steel shaving blades to orient neuronal cells or axons. Additionally, electrodes charged with electrical potential were employed to enhance axon response. Aebischer (8) described an electrically-charged, implantable tubular membrane for use in regenerating severed nerves within the human body. However, none of these devices utilize channels of cell-attractive material, neither do they apply a time varying electromagnetic field, or a static electrical or magnetic field. Additionally, no use is made of simulated or actual microgravity techniques for pure neuronal, or mixed, neuronal and feeder cell cultures. The prior art is deficient in its lack of effective means for growing three dimensional mammalian neuronal tissue in the proximity of, or directly upon the surface, of a current carrying electrode (which may be bioattractive and directly adherent to the cells). Furthermore, the use of a time varying current to induce a corresponding time varying electromagnetic field, in the vicinity of the growing culture, to potentiate or spatially direct cell growth is not part of the prior art.

SUMMARY OF THE INVENTION

The present invention relates to a system and method for culturing biological cells, such as mammalian cells, within a culture medium. The cells are exposed to an electromagnetic field, which, in the preferred embodiment, is a time-varying electromagnetic field. In the preferred embodiment, this field is generated by a conductive electrode, adjacently spaced from the incubating cells, carrying a time varying electrical current. The electrode, in one case, is in direct galvanic contact with the culture media and cells, and in another case, it is placed external to the culture apparatus in a galvanically isolated condition. Preferably, a 10 hertz square wave of 1–6 milliamperes, and with nearly zero time average, is passed through the electrode, suitably from corner to opposite corner of a square metallic conductive plate. The cells, such as neurons in this case, were, in one embodiment, grown directly on the electrode surface, composed of a biocompatable material. In another embodiment, the cells were grown within a container under the influence of a time varying electromagnetic field from an electrode external of and adjacent to the container, galvanically isolated from the media and culture within the container.

The growing cells may actually be attracted and trophically supported by more supportive electrode material or coatings. Furthermore, channels may be incorporated in the culture vessel and lined with growth substrate which may be electrically conductive. In one embodiment, a time varying electromagnetic field is induced in the region of the channel by passing the time varying current through a conductor placed along the channel. This arrangement will further direct growth by the combined effect of the field and trophic materials.

In the preferred embodiment, the presence of the time varying electromagnetic field potentiates the growth of nerve and other tissue. The time varying field may be induced by either: 1) a time varying current within a conductor, or 2) a time varying voltage between fixed conductors. In one embodiment, for example, the culture is placed nearby a conductor through which a time varying current is passed, or between parallel plates upon which a time varying voltage is applied. In both cases, a time varying electromagnetic field results within the area of interest, i.e., in the region of the cell culture.

The system and process are utilized in combination with known tissue culture processes to produce enhanced cell growth, directed cell growth, and tissue formation and organization.

As will be understood from the description to follow, the system is operable to up or down regulate the activity of specific genes. In general, growth promoting genes are up regulated and growth inhibitory genes are down regulated. The effect is shown to persist for some period after termination of the applied time varying field. This persistent, growth promoting effect subsides after a period of some days, and the cells return to a growth state characterized by controls, having never been exposed to the fields. This is beneficial in certain applications, in that medical applications for clinical medical care, i.e. nerve regeneration, are therefore safer than if the "pseudo transformed" state persisted. The set of gene transformations, associated with the time varying electromagnetic field, also promote the ability of the growing tissue to adhere and thrive on substrates by the induction of genes leading to the secretion of extracellular materials favorable to the tissue microenvironment.

Several methods of producing the time varying electromagnetic field in the vicinity of the living tissue culture are encompassed. In one embodiment, an array of conductive current carrying elements (or voltaic electrodes) are arranged so as to intensify or focus the time varying electromagnetic (EM) field onto the culture. Each embodiment is characterized by a method for application of the time varying field to the target tissue, such as neuronal, for stimulation of growth, or repair or induction of changes in gene activity patterns. The term "field generator" is used herein to represent these various embodiments for generating the time varying electromagnetic fields. In its simplest form, it is a conductive electrode, placed near the target cells, through which current is directed from a controlled waveform current source.

As suggested above, in one embodiment, the field generator is in the form of a conductive channel mounted on or embedded in a disc of biocompatable material. (FIG. 11) One or more of these discs may be then placed within a rotational bioreactor so as to obtain the beneficial culture conditions associated therewith. The combination of the stimulatory electromagnetic field with the rotational environment, known to permit morphological expression beyond conventional culture, is particularly effective. This is because the induced pattern of growth enhancing genes is permitted to be ultimately expressed, as cell growth and tissue formation, without mechanical inhibition from the culture apparatus. Also the inherent growth advantages well known in the rotational systems is synergistic with the growth stimulation derived from the time varying electromagnetic field. The conditions may be further optimized by utilizing actual microgravity, in space. In this application, mechanical rotation of the cell culture vessel is not required but may be utilized to achieve mixing and sufficient mass transfer to sustain a healthy culture. Other forms of mixing may be introduced as necessary to achieve adequate mass transfer for each embodiment.

In one embodiment, illustrated in FIGS. 10 and 11, slip-ring contacts or their equivalents are electrically connected to the ends of the channels, and an external power source is provided for applying the time varying electrical current defining the waveform through the channels. In another embodiment, the channel consists of a pair of parallel, mutually spaced conductors across which a time varying voltage is applied. This also achieves the time varying electromagnetic field but restricts it to the region between the parallel electrodes, which is advantageous for directing localized growth according to a desired physical pattern. The present invention also relates to a system and method for culturing primarily two dimensional mammalian cells facilitated by a time varying electromagnetic field. The electrodes may either be in direct galvanic contact or galvanically isolated from the target cells. The present invention provides a strategy to re-engineer nerve tissue and myoneural junctions and can be used medically for axonal regeneration.

In one embodiment of the present invention, there is provided a system for growing three dimensional mammalian cells, comprising a rotating wall vessel containing a cell-rich medium and a formed cell growth substrate. A time varying electromagnetic field is applied to enhance tissue growth which may occur on a shaped substrate. The electromagnetic field may be generated by means such as by directing the current waveform directly through a conductive substrate (or substrate layer) or by projecting the field from an external antenna, or electrode adjacent to and spaced from the medium, the spacing being sufficiently small relative to the strength of the electromagnetic field to induce effectual levels of electromagnetic field within the medium, in accordance with the particular application. A time varying electromagnetic field may be emitted from a nearby plate or other suitable "antennae," or a time varying voltage may be applied across suitable electrodes (such as plates) to produce the time varying electromagnetic field. The field generation system may either be rotating with the vessel or fixed, and spaced from, the rotating vessel. The rotating wall vessel can be a rotating wall perfused vessel or a rotating wall batch-fed vessel.

The time varying electromagnetic field is advantageously produced by a varying electrical potential in the form of a square wave having a frequency of approximately ten cycles per second. In one embodiment, a current of about ten milliamps, conducted between opposite corners of a metallic conductor, produces a stimulatory time varying electromagnetic field extending several centimeters from the plate surface. In practice, the range of frequency and oscillating electromagnetic field strength is a parameter which may be selected to for achieving the desired stimulation of particular tissues, cells, or genes, and for providing the appropriate amount of up/down regulation of these genes.

In one embodiment of the present invention, the cell growth substrates or carriers are spherical disks containing multiple parallel channels (FIG. 10) which are coated with a bioattractive material. The bioattractive material has a longitudinal axis across which the time varying electrical potential is applied and through which a time varying current is conducted. The mammalian cells adhere to the bioattractive material and are free to orient, as they grow. Representative bioattractive materials include titanium, zirconium and platinum.

The class of mammalian cells preferably is selected from the group consisting of neuronal cells, normal human neuronal progenitor cells (NHNP), and a cell responding to the time varying electromagnetic field. It will be understood by those of ordinary skill in the art that the teachings of the present invention apply to other cell types.

In another embodiment of the present invention, there is provided a method of culturing mammalian cells in the claimed system, comprising the steps of inoculating the cells into the vessel containing a culture medium, rotating the vessel to enhance the proliferation of the cells and, in one embodiment, to initiate the attachment of the cells to microcarrier spheres or beads suspended within the culture medium, applying a time varying electromagnetic field to the culture medium, cells, and cell carriers, and measuring the growth of the cells. Preferably, the vessel is rotated at a speed from about 2 RPM to 30 RPM, and the time varying electromagnetic field is generated by a time varying current passed through a conductor with RMS value of about 1 to 1,000 ma. In one embodiment, a range of about 1 mA to 6 mA is used.

In still another embodiment of the present invention, there is provided a system for growing two-dimensional neural cells, comprising a petri dish containing a cell culture medium and an electrode placed in the center of the petri dish. In this embodiment, the electrode serves as the field generator. Preferably, the neural cells are applied directly on the electrode. As a result, the neutral cells exhibit accelerated growth.

In yet another embodiment of the present invention, there is provided a system for growing two-dimensional neural cells further comprising a slide placed on the electrode. Preferably, the neural cells are applied, e.g., bubbled, on the slide instead of directly contacting the electrode, and preferably, the current producing the waveform is applied at a strength range of from about 1 mA to about 100 mA, and, in one embodiment, suitably from about 1 mA to 6 mA.

In still another embodiment of the present invention, there is provided a method of treating an individual having diseased neuronal cells, comprising the steps of growing neuronal cells in the claimed two- or three- dimensional systems and transplanting the neuronal cells into the individual. Such diseases include Parkinson's disease, diseases of neuromuscular junction and Alzheimer's Disease. Neural trauma can also be treated in same methodology.

In yet another embodiment of the present invention, the time varying electromagnetic field (or electrical potential) induces cellular response including cellular control of growth and differentiation at gene level. Preferably, the cellular control of growth and differentiation is to suppress or enhance growth regulatory functions at gene level. Still preferably, the gene is associated with increased tissue and cell proliferation.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
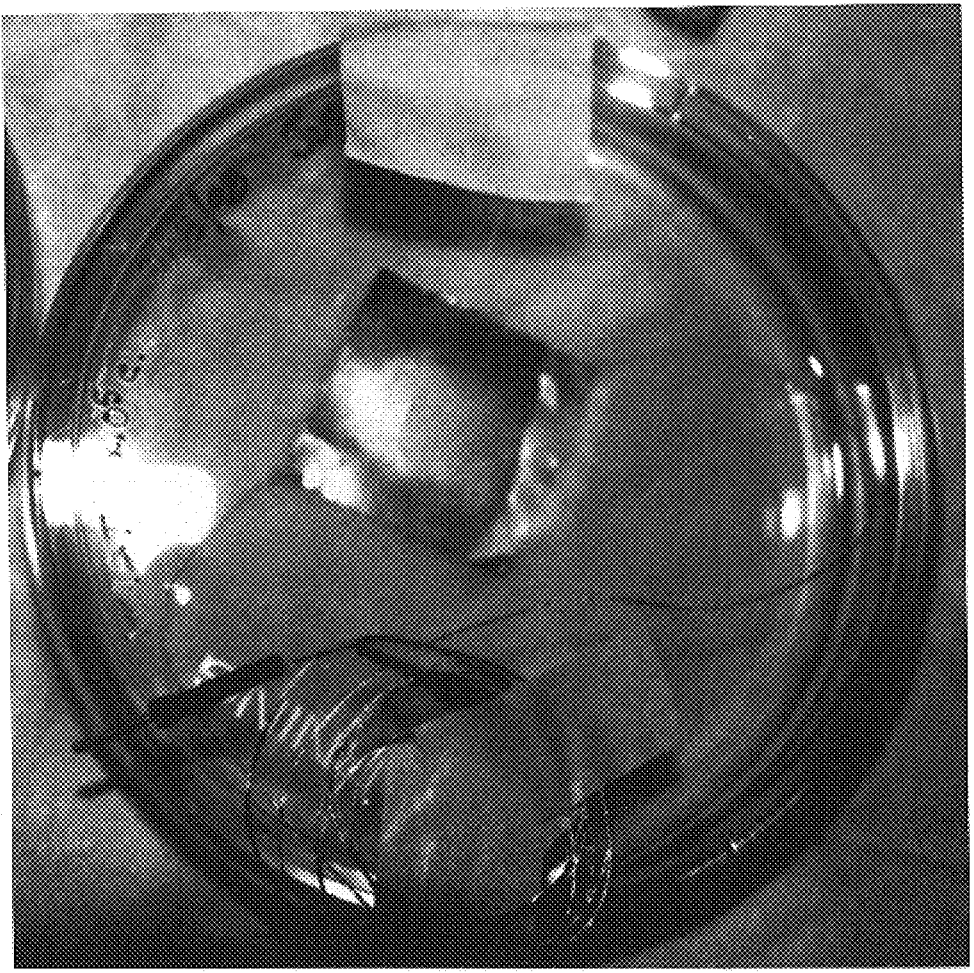
FIG. 1 shows a petri dish with cells in a concentrated bubble placed on the metal electrode in the center of the dish.
Figure 2:
FIG. 2 shows normal human neuronal progenitor (NHNP) cells grown in conventional tissue culture procedures.
Figure 3:
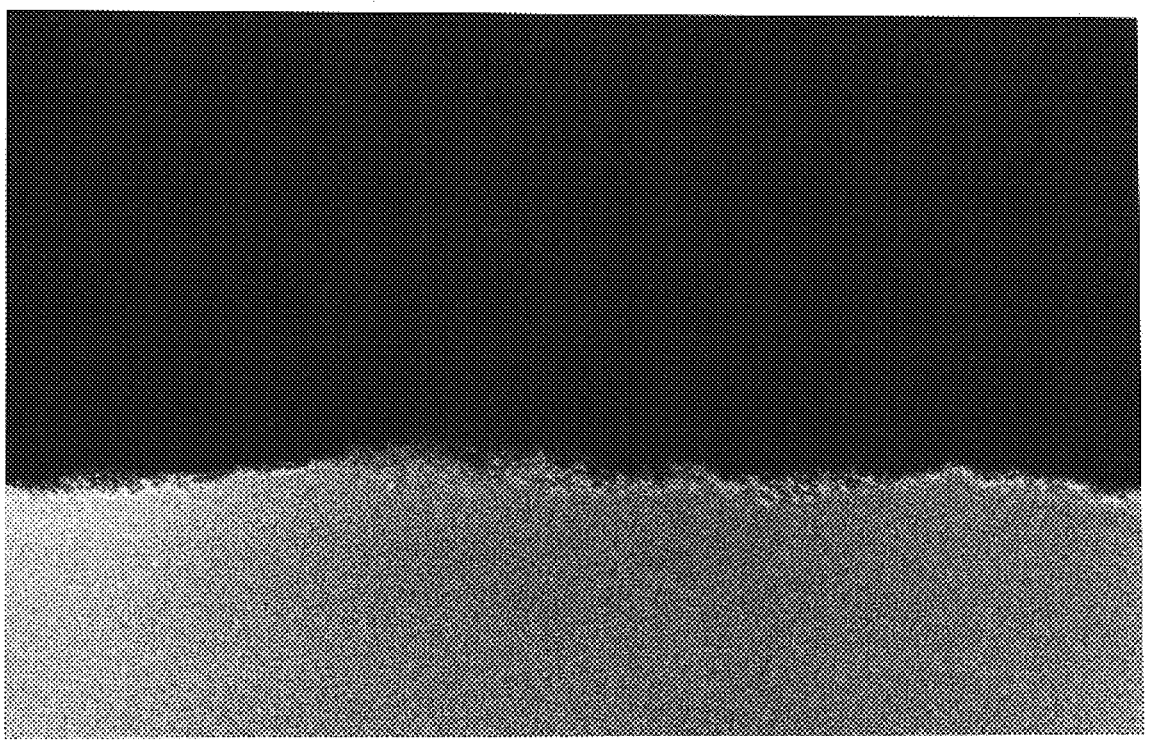
FIG. 3 shows the perimeter of non-waveform influenced normal human neuronal progenitor cells 24 hours after the experiment.
Figure 4:
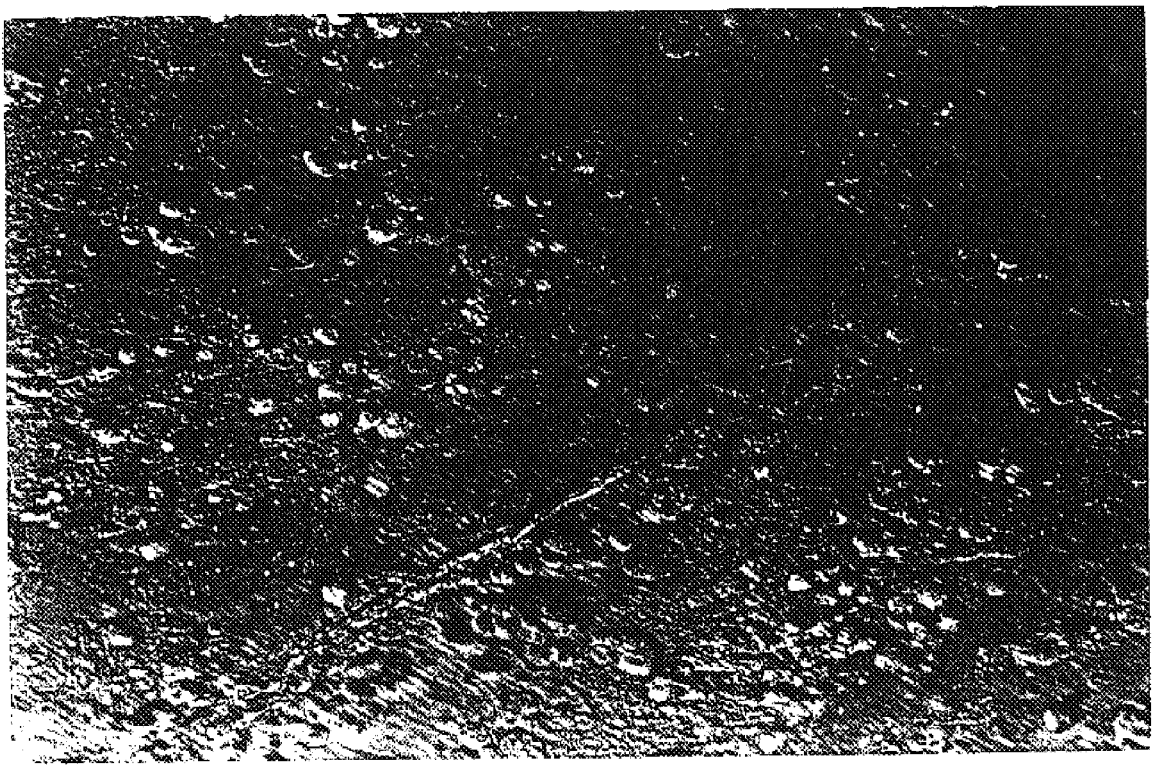
FIG. 4 shows neural tube formation within normal human neuronal progenitor cells under the influence of waveform.
Figure 5:
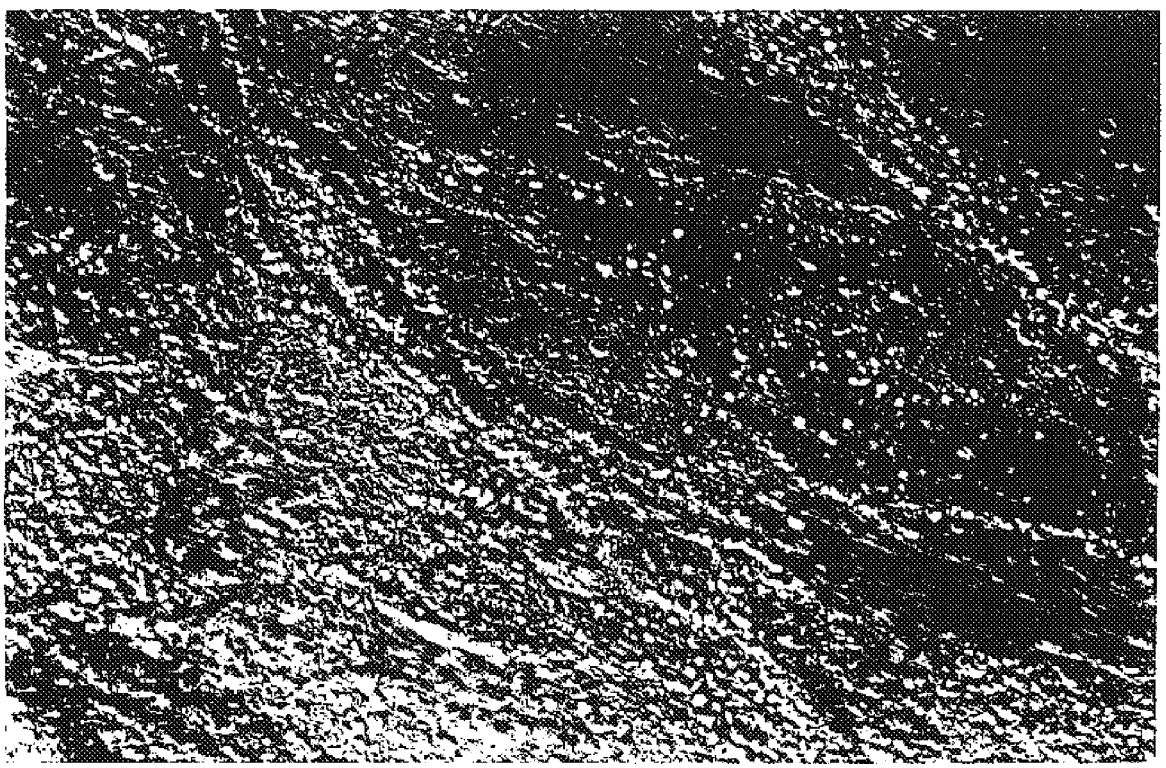
FIG. 5 shows neural tube generation within normal human neuronal progenitor cells under the influence of waveform.
Figure 6:
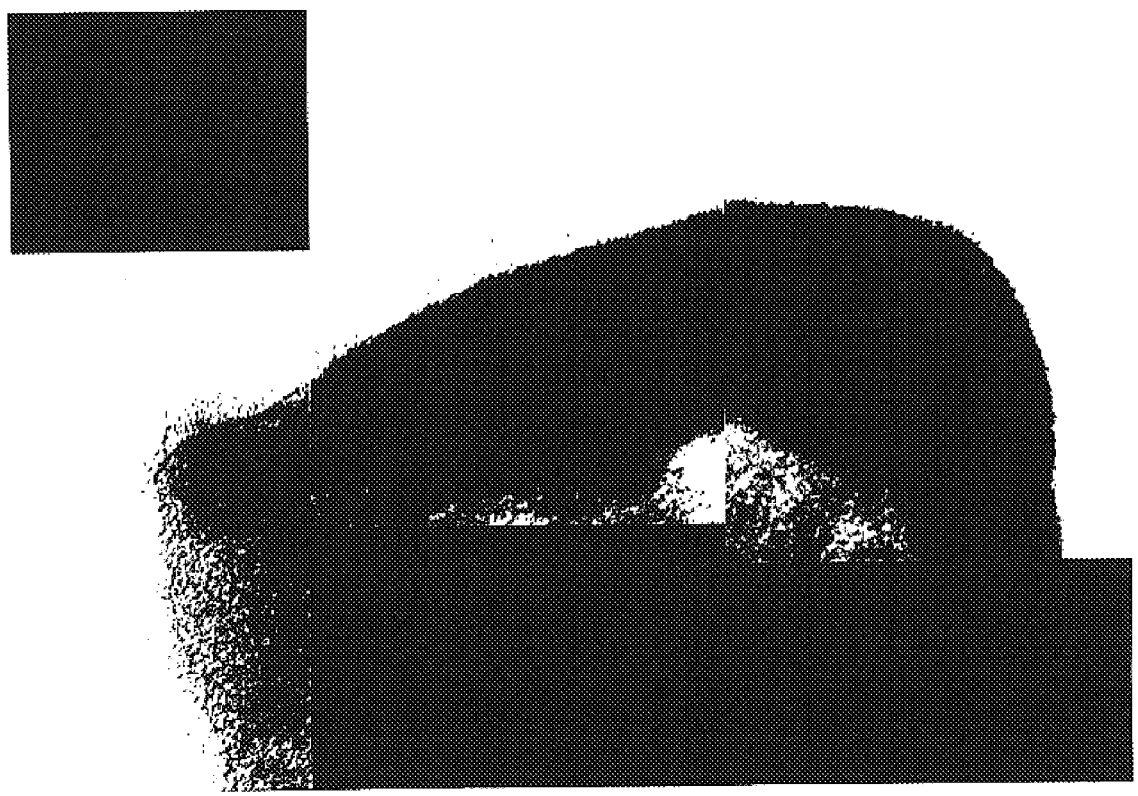
FIG. 6 shows the composition of waveform-influenced neural tissue 24 hours after the exposure.
Figure 7:
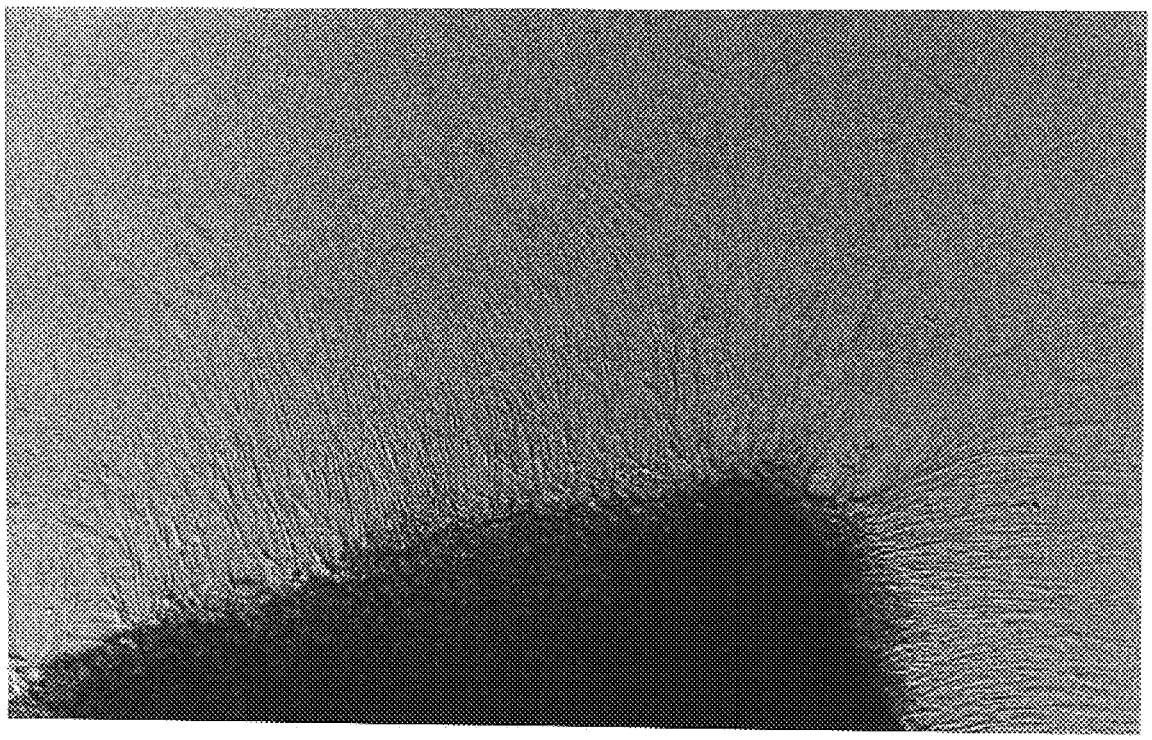
FIG. 7 shows the waveform-influenced normal human neuronal progenitor cells 24 hours after the exposure.
Figure 8:
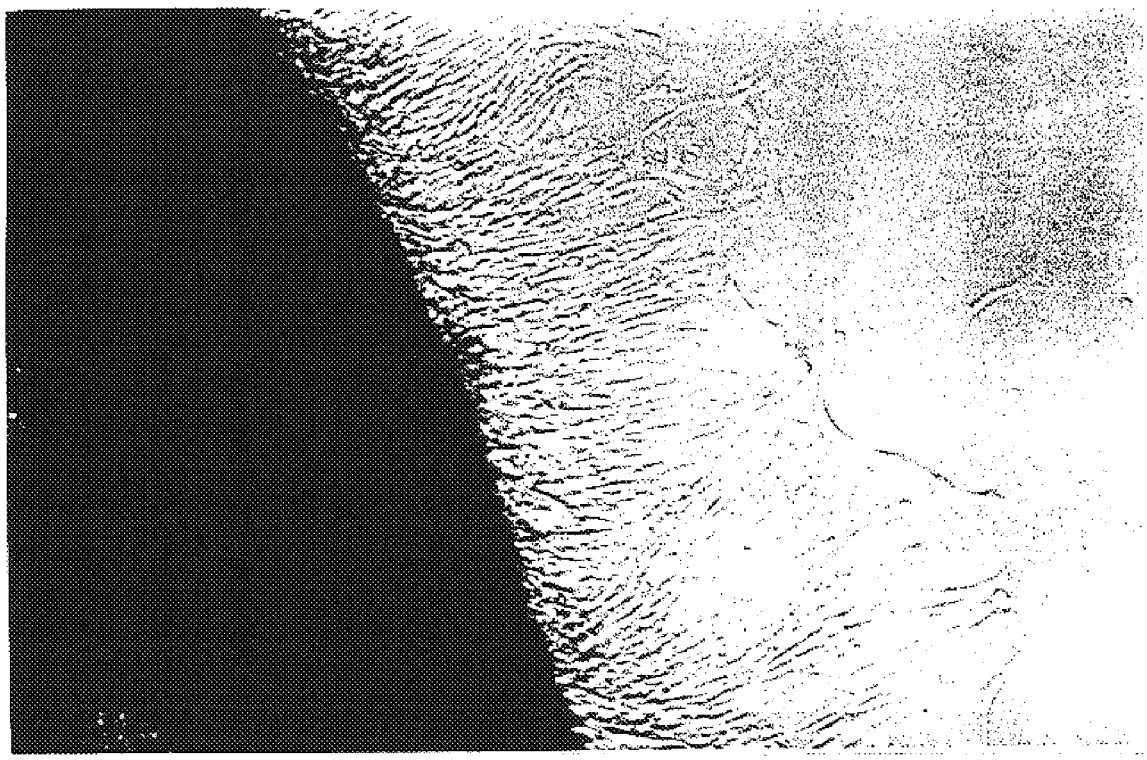
FIG. 8 shows a close-up of waveform-influenced normal human neuronal progenitor cells.
Figure 9:
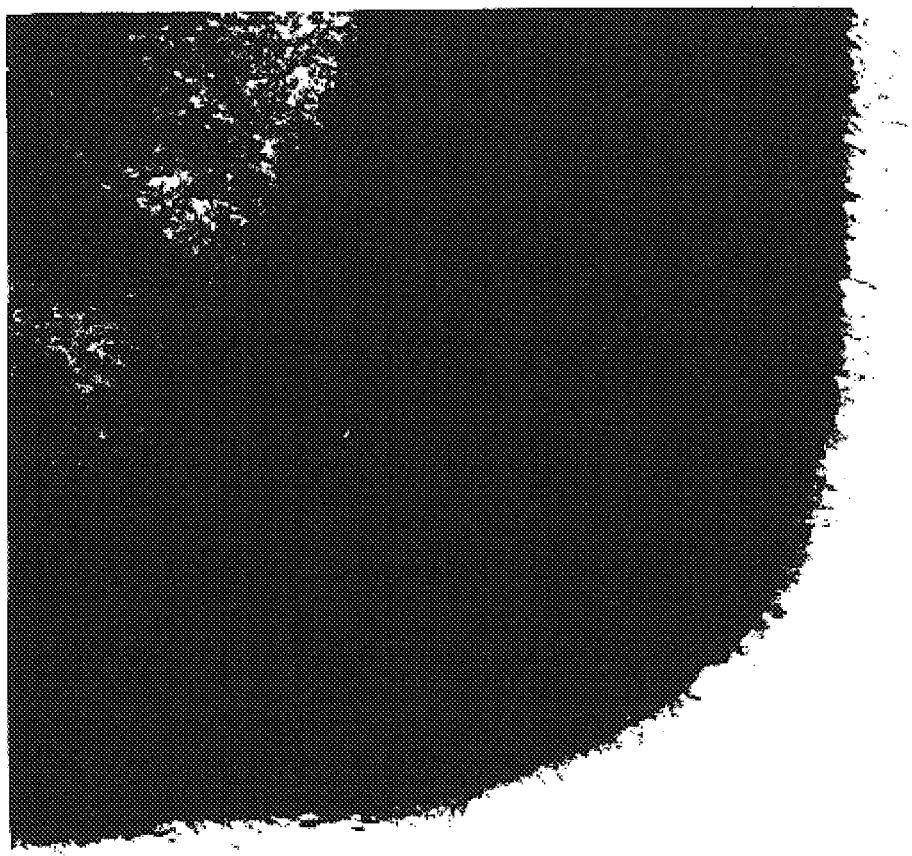
FIG. 9 shows waveform-influenced normal human neuronal progenitor cells 24 hours after the exposure.

As used herein, the term "bioattractive material" shall refer to materials to which a cellular material will attach.

As used herein, the term "longitudinally orient" shall refer to orientation in an elongated cordlike fashion.

As used herein, the term "parallel channels" shall refer to electric channels which are designed to provide constant output to all the electrodes simultaneously.

As used herein, the term "cell carriers" shall refer to microcarrier beads, scaffolds and matrices which support the growth and/or attachment of cellular materials.

As used herein, the term "rotating wall batch-fed vessel" shall refer to slow turning lateral vessel (STLV) and high aspect rotating vessel (HARV).

As used herein, the term "Corona Effect" shall refer to the accelerated growth pattern of neuronal cells electrically potentiated by waveform.

In one preferred embodiment, the present invention is directed to the growth of three dimensional mammalian neuronal tissue using an electrically conductive strip in the form of a channel or mold coated with a bioattractive or biocompatable material to which an electrical potential is applied to longitudinally orient the neural cells or axons as they adhere to the bioattractive material which is suspended in an axon rich medium.

Specifically, in the present embodiment, the apparatus includes a bioreactor chamber vessel employing electrically insulative, biocompatable spherical disks of a material such as silicon. These disks rotate inside the pressure vessel. Each disk has multiple parallel channels cut into its surface. The channels have a semicircular cross-section and contain an electrically conductive inlay in the form of a channel-shaped conductive strip of a bioattractive material such as zirconium, titanium and platinum. Each channel strip 6 has an electrical contact on each longitudinal end that is used to create and control an electrical potential along the length of the strip. The vessel is filled with a medium and the disks are rotated within a medium containing axons. The cells adhere to the electrically conductive bioattractive inlay material. The desired longitudinal cell orientation and therefore the structure of the resulting tissue is affected and/or controlled by the electrical stimulus.

The present invention is also directed to the growth of two dimensional mammalian neuronal tissue using electrodes. The electrodes are either in direct contact or not in contact with the target cells.

In one embodiment of the present invention, there is provided a system for growing three dimensional mammalian cells, comprising a rotating wall vessel containing a cell-rich medium, cell carriers placed within the vessel and an electrical potential applied to the cell carrier. Preferably, the rotating wall vessel can be a rotating wall perfused vessel or a rotating wall batch-fed vessel.

In one embodiment of the present invention, the cell carriers are spherical disks containing multiple parallel channels, which are coated with a bioattractive material. More preferably, the bioattractive material has a longitudinal axis across which the electrical potential is applied. The mammalian cells adhere to the bioattractive material and are therefore oriented longitudinally upon the electrical stimulus. Representative bioattractive materials include titanium, zirconium and platinum.

In the methods of the present invention, the mammalian cell is selected from the group consisting of a neuronal cell, a normal human neuronal progenitor cell (NHNP) and a cell responding to waveform. A person having ordinary skill in this art will be able to apply the teachings of the present invention to other cell types.

In another embodiment of the present invention, there is provided a method of culturing mammalian cells in the claimed system, comprising the steps of inoculating the cells into the vessel, rotating the vessel to initiate the attachment of the cell to the cell carriers, applying an electrical potential to the cell carriers and measuring the growth of the cells. Preferably, the vessel is rotated at a speed from about 10 RPM to 30 RPM, and the electrical potential is applied at a strength range of from about 1 mA to about 6 mA.

In still another embodiment of the present invention, there is provided a system for growing two-dimensional neural cells, comprising a petri dish containing a cell culture medium and an electrode placed in the center of the petri dish. The electrode is charged with a waveform. Preferably, the neural cells are bubbled directly on the electrode. As a result, the neutral cells exhibit accelerated growth.

In yet another embodiment of the present invention, there is provided a system for growing two-dimensional neural cells further comprising a slide placed on the electrode. Preferably, the neural cells are bubbled on the slide instead of directly contacting the electrode. Preferably, the waveform is applied at a strength range of from about 1 mA to about 6 mA.

In still yet another embodiment of the present invention, there is provided a method of treating an individual having diseased neuronal cells, comprising the steps of growing neuronal cells in the two or three dimensional systems disclosed herein and transplanting the grown neuronal cells into the individual. Such diseases include Parkinson's disease, diseases of neuromuscular junction and Alzheimer's Disease. Neural trauma can also be treated with this same methodology.

In yet another embodiment of the present invention, the waveform (or electrical potential) induces a cellular response including cellular control of growth and differentiation at gene level. Preferably, the cellular control of growth and differentiation is to suppress or enhance growth regulatory functions at gene level. Still preferably, the gene is associated with embryogenesis.

The following examples are given for the purpose of illustrating various embodiments of the invention and are not meant to limit the present invention in any fashion.

EXAMPLE 1

Cells

Normal human neuronal progenitor cells (NHNP) were pooled from three donors. As controls, normal human neuronal progenitor cells were grown in conventional tissue culture following standard cell culturing procedures.

EXAMPLE 2

Materials

GTSF-2 medium with 10% FBS, Ciprofloxacin and Fungizone was used to culture the cells. 1×PBS, Collagenase, DNase and Trypsin were purchased from Clonetics. The cells were grown on 12–100 mm Petri dishes (tissue culture coated or not coated). Electrodes were made of platinum and stainless steel. A waveform generator was used to generate the waveform in a strength of 1–6 mA (AC) square wave, 10 Hz variable duty cycle.

EXAMPLE 3

Electrically Potentiating Cell Growth When Electrode is in Direct Contact with the Target Cells Initially, a metal electrode was placed inside a petri dish and centered. Normal human neuronal progenitor cells were seeded at $2\times10^5$ cells in 0.7 ml of media and carefully dropped on the electrode in a concentrated bubble (FIG. 1). Cells were incubated for 2 days. Second day after seeding is considered day 0 of the experiment. At day 0, each dish was given 15 ml of media and waveform was applied to seven electrodes. Cells were observed under a dissecting microscope and fed with 15 ml of media at day 3, and 13 ml every three days at day 6, 9 and 12. At day 14, the cells were fed again with 13 ml of media. At day 17, the cells were incubated for 10 minutes in a Collagenase/DNase cocktail, then trypsin was directly applied to the cocktail and the cells were further incubated for 3 more minutes. Before the media was added to deactivate trypsin, the cocktail mix was pipetted up and down several times. The cells were washed twice with 1×PBS, reapplied with the media and placed on ice. The cells were counted, assessed for viability.

To examine the accelerated growth of cells 48 and 72 hours after waveform was discontinued, cells were treated the same as above, except that after day 14 treatment, instead of harvesting, two dishes from the non-waveform group (control) and two dishes from the waveform group were randomly chosen and re-seeded at $9\times10^5$ cells in two new petri dishes each, with a total of four dishes. Cells from one set (#11 waveform and control #6) were counted and photographed 48 hours after seeding, and cells from the second set (#12 waveform and control #7) were counted and photographed 72 hours after seeding.

To examine accelerated growth pattern "Corona Effect" after the electrical potentiation, the same treatment was applied to the cells without harvesting. A dish each from waveform group and non-waveform group were chosen randomly. Cells still attached in sheet from were lifted off of the electrodes carefully and placed in new petri dishes with medium, and then photographed 24 hours later.

EXAMPLE 4

Electrically Potentiating Cell Growth When Electrode is not in Direct Contact with the Target Cells Initially, a metal electrode was placed inside a petri dish and centered. A slide was carefully placed on the electrode under sterile conditions. Normal human neuronal progenitor cells were seeded at $2 \times 10^5$ cells in 0.7 ml of media and bubbled on the slide. Cells were incubated for 2 days. 25 ml of media were applied and two 1000 $\mu$l pipetman blue tips were placed in the dish to anchor the slide to bottom of the dish. The second day after seeding was considered day 0 of the experiment. At day 0, each dish was given 25 ml of media and waveform was applied to six of the twelve electrodes.

Cells were observed under a dissecting microscope and fed with 25 ml of media every three days at day 3, 6, 9 and 12. At day 14, the cells were fed again with 25 ml of media. At day 18, the cells were incubated for 10 minutes in a Collagenase/DNase cocktail, then typsin was directly applied to the cocktail and the cells were further incubated for 3 more minutes. Before the media was added to deactivate trypsin, the cocktail mix was pipetted up and down several times. The cells were washed twice with 1×PBS, reapplied with the media and placed on ice. The cells were counted, assessed for viability and then replated at 100,000 per plate. The remaining waveform and non waveform slides were fixed and refrigerated for staining at a later date.

EXAMPLE 5

Electrically Potentiated Growth of Cells

Normal human neuronal progenitor-pool cells exposed to a time varying electromagnetic field (waveform), either in direct contact or not in direct contact with the electrode, displayed an accelerated growth rate and different morphology as compared to non waveform cells (control), i.e., cells not subject to the time varying electromagnetic field (see Table 1 and Table 2, FIGS. 2–9). After the application of the time varying electromagnetic field or waveform, the cells preferentially aligned, while cells without waveform exposure showed random pattern. Cells in direct contact with the electrode remained stimulated up to at least 72 hours after waveform was removed (Table 3); while those not in direct contact with the electrode once removed from waveform continued to experience accelerated and long term stimulation growth pattern even after 168 hours (Table 4). Viability was also higher in the cells exposed to the waveform (Table 4). Cells were suspended easily with the Collagenase/DNase then trypsin sequence.

TABLE 1

*Cell Count and Viability at Harvest (day 17)

| NHNP-POOL | CELL COUNT | VIABILITY | HARVEST |
| --- | --- | --- | --- |
| Waveform 1 | 860,000 | 98% | 17 days |
| Waveform 2 | 1,000,000 | 98% | 17 days |
| Waveform 3 | 1,000,000 | 98% | 17 days |
| Waveform 4 | 1,300,000 | 98% | 17 days |
| Waveform 7 | 1,000,000 | 98% | 17 days |
| Waveform 8 | 940,000 | 98% | 17 days |
| Waveform 9 | 700,000 | 98% | 17 days |
| Waveform 10 | 1,000,000 | 98% | 17 days |
| Control 1 | 500,000 | 98% | 17 days |
| Control 2 | 400,000 | 98% | 17 days |
| Control 3 | 300000 | 98% | 17 days |
| Control 4 | 500,000 | 98% | 17 days |
| Control 5 | 400,000 | 98% | 17 days |

*Cells were in direct contact with the electrode.

TABLE 2

*Cell Count and Viability at Harvest (day 18)

| NHNP-POOL | CELL COUNT | VIABILITY | HARVEST |
| --- | --- | --- | --- |
| Waveform 1 | 1,000,000 | 100% | 18 days |
| Waveform 5 | 1,100,000 | 100% | 18 days |
| Control 1 | 800,000 | 100% | 18 days |
| Control 5 | 800,000 | 100% | 18 days |

*Cells were not in direct contact with the electrode.

TABLE 3

*Cell Count at Various Times after Removal of Waveform

| CELLS | COUNT | HOURS OFF ELECTRODE |
| --- | --- | --- |
| Waveform 11 | 520,000 | Counted and re-seeded at 96,000/plate |
| Control 6 | 112,000 | Counted and re-seeded at 96,000/plate |
| Waveform 11 | 274,000 | 48 hours off electrode |
| Control 6 | 48,000 | 48 hours off electrode |
| Waveform 12 | 576,000 | Counted and re-seeded at 96,000/plate |
| Control 7 | 96,000 | Counted and re-seeded at 96,000/plate |
| Waveform 12 | 228,000 | 72 hours off electrode |
| Control 7 | 120,000 | 72 hours off electrode |

*Cells were in direct contact with the electrode.

TABLE 4

*Cell Count and Viability at Various Times after Harvest

| NHNP-POOL | CELL COUNT | VIABILITY | TIME AFTER HARVEST (Hours) |
| --- | --- | --- | --- |
| Waveform 1 | 56,000 | 85% | 24 |
| Waveform 5 | 40,000 | 85% | 24 |
| Control 1 | 36,000 | 65% | 24 |
| Control 5 | 28,000 | 65% | 24 |
| Waveform 1 | 188,000 | 98% | 48 |
| Waveform 5 | 212,000 | 98% | 48 |
| Control 1 | 74,000 | 87% | 48 |
| Control 5 | 162,000 | 90% | 48 |
| Waveform 1 | 3,400,000 | 100% | 120 |
| Waveform 5 | 3,400,000 | 100% | 120 |
| Control 1 | 900,000 | 99% | 120 |
| Control 5 | 900,000 | 99% | 120 |
| Waveform 1 | 4,000,000 | 100% | 168 |
| Waveform 5 | 3,800,000 | 100% | 168 |

TABLE 4-continued

*Cell Count and Viability at Various Times after Harvest

| NHNP-POOL | CELL COUNT | VIABILITY | TIME AFTER HARVEST (Hours) |
|---|---|---|---|
| Control 1 | 980,000 | 97% | 168 |
| Control 5 | 900,000 | 95% | 168 |

*Cells were not in direct contact with the electrode.

EXAMPLE 6

Waveform Gene Array Display (GAD) Results

Normal Human Neural Progenitor cells or human adult astrocytes were exposed to waveform and non-waveform growth conditions for 17 days. Upon completion of the exposure period cells were harvested via trypsinization and poly-RNA was prepared from the respective groups of cells. RNA samples were quick frozen and shipped to Synteni Corporation for GAD analysis. Below are the results of a survey of the response of over 10,000 human genes. The results were divided into two categories (Table 5 and Table 6). Those genes down regulated or suppressed by the waveform and those up regulated or enhanced in activity by the waveform.

An analysis of the data indicates a significant down regulation of maturation and regulatory genes. These maturation and regulatory genes are normally associated with the differentiated or non-growth profile of normal cells. However, there is a significant up regulation of some 150 genes which are mainly associated with growth and cellular proliferation. Neither two nor three dimensional growth of neural cells has been achieved prior to this event with the positive outcome of enhanced growth and apparent gene regulatory control.

TABLE 5

Down Regulated Genes in Descending Order (Highest to lowest)

1. *Homo sapiens* (clone Zap2) mRNA fragment {Incyte PD:1661837}
2. CDC28 protein kinase 2 {Incyte PD:1384823}
3. Synteni: YCFR 22 {YC 22.2000.W}
4. ESTs, Moderately similar to cell growth regulating nucleolar protein LYAR [*M.musculus*]{Incyte PD:2233551}
5. KERATIN, TYPE II CYTOSKELETAL 7 {Incyte PD:1649959}
6. MITOTIC KINESIN-LIKE PROTEIN-1 {Incyte PD:2640427}
7. EST {Incyte PD:674714}
8. Synteni: YCFR 22 {YC 22.2000.X}
9. Synteni: YCFR 26 {YC 26.0062.N}
10. Synteni: YCFR 22 {YC 22.2000.Z}
11. Transcription factor 6-like 1 (mitochondrial transcription factor 1-like) {Incyte PD:3371995}
12. Interferon-inducible 56-KDa protein {Incyte PD:1215596}
13. EST {Incyte PD:1794375}
14. *Homo sapiens* mitotic feedback control protein Madp2 homolog mRNA, complete cds {Incyte PD:2414624}
15. EST {Incyte PD:151026}
16. *Homo sapiens* Pig3 (PIG3) mRNA, complete cds {Incyte PD:2395269}
17. General transcription factor IIIA {Incyte PD:1527070}
18. Cellular retinoic acid-binding protein [human, skin, mRNA, 735 nt] {Incyte PD:585432}
19. EST {Incyte PD:1755159}
20. *Homo sapiens* mRNA for KIAA0285 gene, complete cds {Incyte PD:1738053}
21. ESTs, Weakly similar to F25H5.h [*C.elegans*] {Incyte PD:1923567}

TABLE 5-continued

Down Regulated Genes in Descending Order (Highest to lowest)

22. *Homo sapiens* mRNA expressed in osteoblast, complete cds {Incyte PD:2537863}
23. EST {Incyte PD:3204745}
24. *Homo sapiens* mRNA for serine/threonine protein kinase SAK {Incyte PD:2732630}
25. *Homo sapiens* serum-inducible kinase mRNA, complete cds {Incyte PD:1255087}
26. Carbonic anhydrase II {Incyte PD:2474163}
27. EST {Incyte PD:660376}
28. GRANCALCIN {Incyte PD:1671852}
29. N-CHIMAERIN {Incyte PD:1852659}
30. *Homo sapiens* Pig10 (PIG10) mRNA, complete cds {Incyte PD:1731061}
31. Adenylosuccinate lyase {Incyte PD:1653326}
32. EST {Incyte PD:1798393}
33. *Homo sapiens* HP protein (HP) mRNA, complete cds {Incyte PD:3084122}
34. ESTs, Moderately similar to T10C6.i [*C.elegans*] {Incyte PD:1923186}
35. Chromosome condensation 1 {Incyte PD:3180854}
36. Calmodulin 1 (phosphorylase kinase, delta) {Incyte PD:2803306}
37. Centromere protein A (17kD) {Incyte PD:2444942}
38. V-jun avian sarcoma virus 17 oncogene homolog {Incyte PD:1920177}
39. Human glutathione-S-transferase homolog mRNA, complete cds {Incyte PD:1862232}
40. *Homo sapiens* gene for protein involved in sexual development, complete cds {Incyte PD:3033934}
41. EST {Incyte PD:2630992}
42. Human low-Mr GTP-binding protein (RAB32) mRNA, partial cds {Incyte PD:1662688}
43. Annexin III (lipocortin III) {Incyte PD:1920650}
44. Hydroxymethylbilane synthase {Incyte PD:1509204}
45. Synteni: HK 4 {HK 4.2000.Y}
46. Ribosomal protein L7a {Incyte PD:2579602}
47. Human mRNA for myosin regulatory light chain {Incyte PD:78783}
48. Ferredoxin reductase {Incyte PD:1819763}
49. Human copper transport protein HAH1 (HAH1) mRNA, complete cds {Incyte PD:2313349}
50. Human G protein gamma-11 subunit mRNA, complete cds {Incyte PD:1988432}
51. Synteni: HK 4 {HK 4.2000.W}
52. Human XIST, coding sequence a mRNA (locus DXS399E) {Incyte PD:1514318}
53. Ribosomal protein, large, P0 {Incyte PD:3511355}
54. *Homo sapiens* clone 23714 mRNA sequence {Incyte PD:1728368}
55. Human mRNA for Apol_Human (MER5(Aopl-Mouse)-like protein), complete cds {Incyte PD:2527879}
56. Synteni: HK 4 {HK 4.2000.Z}
57. Proteasome (prosome, macropain) subunit, beta type, 5 {Incyte PD:2503119}
58. Human PINCH protein mRNA, complete cds {Incyte PD:126888}
59. *Homo sapiens* peroxisome assembly protein PEX10 mRNA, complete cds {Incyte PD:998279}
60. *Homo sapiens* short chain L-3-hydroxyacyl-CoA dehydrogenase (SCHAD) mRNA, complete cds {Incyte PD:1638850}
61. Neuroblastoma RAS viral (v-ras) oncogene homolog {Incyte PD:2816984}
62. *H.sapiens* mRNA for b4 integrin interactor {Incyte PD:1932850}
63. Human forkhead protein FREAC-1 mRNA, complete cds {Incyte PD:1449920}
64. Human mRNA for protein D123, complete cds {Incyte PD:1920522}
65. *H.sapiens* mRNA for A-kinase anchoring protein AKAP95 {Incyte PD:1628787}
66. Carbonyl reductase {Incyte PD:1633249}
67. EST {Incyte PD:2060973}
68. ESTs, Highly similar to GUANINE NUCLEOTIDE-BINDING PROTEIN G(I)/G(S)/G(O) GAMMA-7 SUBUNIT [*Rattus norvegicus*] {Incyte PD:1640161}
69. *Homo sapiens* Na+/Ca+ exchanger mRNA sequence {Incyte PD:2880435}
70. STRESS-ACTIVATED PROTEIN KINASE JNK1 {Incyte PD:3331719}

TABLE 5-continued

Down Regulated Genes in Descending Order (Highest to lowest)

71. *Homo sapiens* leupaxin mRNA, complete cds {Incyte PD: 1595756}
72. CLEAVAGE SIGNAL-1 PROTEIN {Incyte PD:2054053}
73. EST {Incyte PD:1798965}
74. Human DNA from overlapping chromosome 19 cosmids R31396, F25451, and R31076 containing COX6B and UPKA, genomic sequence {Incyte PD:1320685}
75. INTERFERON-INDUCED 17 KD PROTEIN {Incyte PD: 2862971}
76. Human homolog of yeast IPP isomerase {Incyte PD:1526240}
77. Translation elongation factor 1 gamma {Incyte PD:3138196}
78. Tropomyosin alpha chain (skeletal muscle) {Incyte PD:1572555}
79. Aplysia ras-related homolog 9 {Incyte PD:2733928}
80. ATP SYNTHASE ALPHA CHAIN, MITOCHONDRIAL PRECURSOR {Incyte PD:3206210}
81. *Homo sapiens* androgen receptor associated protein 24 (ARA24) mRNA, complete cds {Incyte PD:552654}
82. Glucagon {Incyte PD:1333075}
83. Human enhancer of rudimentary homolog mRNA, complete cds {Incyte PD:1704472}
84. TRANSCRIPTIONAL ENHANCER FACTOR TEF-1 {Incyte PD:2957175}
85. Ubiquitin-like protein {Incyte PD:1754454}
86. Human RGP4 mRNA, complete cds {Incyte PD:617517}
87. Cellular retinol-binding protein {Incyte PD:1612969}
88. Ornithine decarboxylase 1 {Incyte PD:1930235}
89. EST {Incyte PD:3605632}
90. EST {Incyte PD:2057260}
91. ESTs, Weakly similar to CAMP-DEPENDENT PROTEIN KINASE TYPE 2 [*Saccharomyces cerevisiae*] {Incyte PD:2055611}
92. Human p37NB mRNA, complete cds {Incyte PD:1407110}
93. Human mRNA for suppressor for yeast mutant, complete cds {Incyte PD:2888814}
94. EST {Incyte PD:3142705}
95. ESTs, Weakly similar to K01H12.1 [*C.elegans*] {Incyte PD:56197}
96. Cell division cycle 2, G1 to S and G2 to M {Incyte PD:1525795}
97. EST {Incyte PD:1794175}
98. EST {Incyte PD:1489557}
99. ESTs, Weakly similar to PROTEIN PHOSPHATASE PP2A, 72 KD REGULATORY SUBUNIT [*H. sapiens*] {Incyte PD:2379045}
100. CAMP-DEPENDENT PROTEIN KINASE TYPE II-ALPHA REGULATORY CHAIN {Incyte PD:1649731}
101. ESTs, Weakly similar to transcription factor [*H.sapiens*] {Incyte PD:1637517}
102. ATP synthase, H+ transporting, mitochondrial F1 complex, O subunit (oligomycin sensitivity conferring protein) {Incyte PD:2193246}
103. RAS-LIKE PROTEIN TC21 {Incyte PD:2505425}
104. Small nuclear ribonucleoprotein polypeptides B and B1 {Incyte PD:2071473}
105. EST {Incyte PD:1922084}
106. Proliferating cell nuclear antigen {Incyte PD:2781405}
107. ESTs, Highly similar to HIGH MOBILITY GROUP-LIKE NUCLEAR PROTEIN 2 [*Saccharomyces cerevisiae*] {Incyte PD:2669174}
108. EST {Incyte PD:1844150}
109. Human mRNA for proteasome subunit HsC10-II, complete cds {Incyte PD:1737833}
110. *Homo sapiens* mRNA for ST1C2, complete cds {Incyte PD:3993007}
111. Human dual specificity phosphatase tyrosine/serine mRNA, complete cds {Incyte PD:1514573}
112. Human stimulator of TAR RNA binding (SRB) mRNA, complete cds {Incyte PD:2057162}
113. EST {Incyte PD:2507206}
114. *H.sapiens* mRNA for Ndr protein kinase {Incyte PD:3318571}
115. ESTs, Weakly similar to Grb2-related adaptor protein [*H.sapiens*] {Incyte PD:1857259}
116. ESTs, Highly similar to Tbc1 [*M.musculus*] {Incyte PD:1889147}
117. GTPase-activating protein ras p21 (RASA) {Incyte PD:147344}
118. Human mRNA for KIAA0123 gene, partial cds {Incyte PD:1752436}
119. Synteni: YCFR 22 {YC 22.2000.Y}
120. Human non-histone chromosomal protein (NHC) mRNA, complete cds {Incyte PD:1748670}
121. Thioredoxin {Incyte PD:2606240}
122. FATTY ACID-BINDING PROTEIN, EPIDERMAL {Incyte PD:2537805}
123. Proteasome component C2 {Incyte PD:2195309}
124. *Homo sapiens* heat shock protein hsp40 homolog mRNA, complete cds {Incyte PD:2844989}
125. Human amyloid precursor protein-binding protein 1 mRNA, complete cds {Incyte PD:1663083}
126. *Homo sapiens* DNA binding protein homolog (DRIL 1) mRNA, complete cds {Incyte PD:2538333}
127. Human Has2 mRNA, complete cds {Incyte PD:3602403}
128. EST {Incyte PD:1749678}
129. *Homo sapiens* golgi SNARE (GS27) mRNA, complete cds {Incyte PD:3279439}
130. ESTs, Weakly similar to UBIQUITIN-ACTIVATING ENZYME E1 HOMOLOG [*H.sapiens*] {Incyte PD:1710472}
131. Synteni: YCFR 22 {YC 22.2000.N}
132. Voltage-dependent anion channel 2 {Incyte PD:2189062}
133. Human rap2 mRNA for ras-related protein {Incyte PD:3334979}
134. Acid phosphatase 1, soluble {Incyte PD:620871}
135. Human clone 23840 mRNA, partial cds {Incyte PD:1830083}
136. Human mRNA for KIAA0008 gene, complete cds {Incyte PD:1970111}
137. *H.sapiens* mRNA for protein-tyrosine-phosphatase (tissue type: foreskin) {Incyte PD:444957}
138. Human B-cell receptor associated protein (hBAP) mRNA, partial cds {Incyte PD:2545562}
139. ESTs, Highly similar to ring finger protein [*H.sapiens*] {Incyte PD:2860918}
140. *H.sapiens* mRNA for CLPP {Incyte PD:2675481}
141. APOPTOSIS REGULATOR BCL-X {Incyte PD:1855683}
142. PROTEASOME COMPONENT C13 PRECURSOR {Incyte PD:2668334}
143. Sorting nexin 1 {Incyte PD:1508407}
144. Human voltage dependent anion channel form 3 mRNA, complete cds {Incyte PD:2051154}
145. *H.sapiens* mRNA for translin {Incyte PD:986855}
146. Human DEAD-box protein p72 (P72) mRNA, complete cds {Incyte PD:1750553}
147. Ras homolog gene family, member G (rho G) {Incyte PD:1342744}
148. EST {Incyte PD:1377794}
149. Human FEZ2 mRNA, partial cds {Incyte PD:2623268}
150. Human homolog of Drosophila discs large protein, isoform 2 (hdlg-2) mRNA, complete cds {Incyte PD:2203554}
151. ALCOHOL DEHYDROGENASE {Incyte PD:1634342}
152. 3-hydroxymethyl-3-methylglutaryl-Coenzyme A lyase (hydroxymethylglutaricaciduria) {Incyte PD:1695917}
153. ENOYL-COA HYDRATASE, MITOCHONDRIAL PRECURSOR {Incyte PD:2235870}
154. Proteasome (prosome, macropain) subunit, beta type, 6 {Incyte PD:2989852}
155. INTERFERON GAMMA UP-REGULATED I-5111 PROTEIN PRECURSOR {Incyte PD:2211625}
156. Epimorphin {Incyte PD:3438987}
157. *H.sapiens* RY-1 mRNA for putative nucleic acid binding protein {Incyte PD:1805712}
158. EST {Incyte PD:1905120}
159. KD HOUSEKEEPING PROTEIN {Incyte PD:1819287}
160. Cytochrome c oxidase subunit VIIb {Incyte PD:2060789}
161. EST {Incyte PD:661516}
162. *Homo sapiens* nuclear VCP-like protein NVLp.2 (NVL.2) mRNA, complete cds {Incyte PD:1445507}
163. EST {Incyte PD:1251588}
164. EST {Incyte PD:1665871}
165. *Homo sapiens* inositol polyphosphate 4-phosphatase type II-alpha mRNA, complete cds {Incyte PD:3032739}
166. *Homo sapiens* arsenite translocating ATPase (ASNA1) mRNA, complete cds {Incyte PD:1666094}
167. Human SnRNP core protein Sm D3 mRNA, complete cds {Incyte PD:1624865}
168. *Homo sapiens* clone 23777 putative transmembrane GTPase mRNA, partial cds {Incyte PD:2554541}
169. *Homo sapiens* regulator of G protein signaling RGS12 (RGS) mRNA, complete cds {Incyte PD:3618382}

TABLE 5-continued

Down Regulated Genes in Descending Order (Highest to lowest)

170. Human Ki nuclear autoantigen mRNA, complete cds {Incyte PD:1308112}
171. *Homo sapiens* peroxisomal phytanoyl-CoA alpha-hydroxylase (PAHX) mRNA, complete cds {Incyte PD:4073867}
172. PLACENTAL CALCIUM-BINDING PROTEIN {Incyte PD:1222317}
173. PRE-MRNA SPLICING FACTOR SF2, P32 SUBUNIT PRECURSOR {Incyte PD:1552335}
174. Human clone C4E 1.63 (CAC)n/(GTG)n repeat-containing mRNA {Incyte PD:1928789}
175. Human glioma pathogenesis-related protein (GliPR) mRNA, complete cds {Incyte PD:477045}
176. Homeo box A9 {Incyte PD:459651}

TABLE 6

Waveform Up Regulated Genes in Ascending Order (Lowest to Highest)

1. NEUROMEDIN B PRECURSOR {Incyte PD:2754315}
2. Synteni: YCFR 21 {YC 21.0031.N}
3. ATRIAL NATRIURETIC PEPTIDE CLEARANCE RECEPTOR PRECURSOR {Incyte PD:1353606}
4. Synteni: YCFR 85 {YC 85.2000.Y}
5. *Homo sapiens* CHD3 mRNA, complete cds {Incyte PD:1965248}
6. EST {Incyte PD:565872}
7. Synteni: YCFR 46 Cy3 {YC 46.2000.Z}
8. ESTs, Weakly similar to metaxin [*H.sapiens*] {Incyte PD:1754461}
9. Plasminogen {Incyte PD:2515873}
10. Human mRNA for CC chemokine LARC precursor, complete cds {Incyte PD:2220923}
11. Synteni: YCFR 21 {YC 21.0062.N}
12. *Homo sapiens* Amplified in Breast Cancer (AIB1) mRNA, complete cds {Incyte PD:2634478}
13. *Homo sapiens* clone 24640 mRNA sequence {Incyte PD:1560143}
14. Synteni: YCFR 21 {YC 21.2000.N}
15. EST {Incyte PD:143912}
16. Human transcription factor SIM2 long form mRNA, complete cds {Incyte PD:996104}
17. EST {Incyte PD:2841478}
18. PUTATIVE DNA BINDING PROTEIN A20 {Incyte PD:1878791}
19. Protein tyrosine phosphatase, receptor type, mu polypeptide {Incyte PD:987736}
20. Human clone A9A2BRB5 (CAC)n/(GTG)n repeat-containing mRNA {Incyte PD:1987975}
21. Endothelin converting enzyme 1 {Incyte PD:1963819}
22. BB1 {Incyte PD:1966148}
23. Pleiotrophin (heparin binding growth factor 8, neurite growth-promoting factor 1) {Incyte PD:2989411}
24. Argininosuccinate synthetase {Incyte PD:1981145}
25. Human breast epithelial antigen BA46 mRNA, complete cds {Incyte PD:1319020}
26. Human clone 46690 brain expressed mRNA from chromosome X {Incyte PD:1669780}
27. Human plectin (PLEC1) mRNA, complete cds {Incyte PD:1907232}
28. *Homo sapiens* mRNA for calmegin, complete cds {Incyte PD:2498216}
29. EST {Incyte PD:769182}
30. Amyloid beta (A4) precursor-like protein 2 {Incyte PD:3876715}
31. Polymerase (RNA) II (DNA directed) polypeptide A (220kD) {Incyte PD:1382059}
32. GLUCOSE TRANSPORTER TYPE 3, BRAIN {Incyte PD:2745082}
33. *Homo sapiens* sarco-/endoplasmic reticulum Ca-ATPase 3 (ATP2A3) mRNA, alternatively spliced, partial cds {Incyte PD:688411}
34. Human c-jun proto oncogene (JUN), complete cds, clone hCJ-1 {Incyte PD:1969563}
35. Microtubule-associated protein 1A {Incyte PD:702684}
36. Clusterin (complement lysis inhibitor; testosterone-repressed prostate message 2; apolipoprotein J) {Incyte PD:2966620}
37. NADH-CYTOCHROME B5 REDUCTASE {Incyte PD:1901142}

TABLE 6-continued

Waveform Up Regulated Genes in Ascending Order (Lowest to Highest)

38. Protein-tyrosine kinase 7 {Incyte PD:996229}
39. Alpha-1 type XVI collagen {Incyte PD:1963529}
40. EST {Incyte PD:2839121}
41. *Homo sapiens* mRNA for DEC1, complete cds {Incyte PD:1732479}
42. Human endogenous retroviral protease mRNA, complete cds {Incyte PD:1347636}
43. ATPase, Na+/K+ transporting, alpha 1 polypeptide {Incyte PD:1730609}
44. Laminin, alpha 4 {Incyte PD:1851696}
45. Hexabrachion (tenascin C, cytotactin) {Incyte PD:1453450}
46. Human mRNA for KIAA0325 gene, partial cds {Incyte PD:1995315}
47. Integrin beta-5 subunit {Incyte PD:418731}
48. Microfibrillar-associated protein 4 {Incyte PD:1659231}
49. Fibulin 1 {Incyte PD:1320658}
50. Protein serine/threonine kinase stk2 {Incyte PD:1518981}
51. ESTs, Weakly similar to HYPOTHETICAL 16.1 KD PROTEIN IN SEC 17-QCR1 INTERGENIC REGION [*Saccharomyces cerevisiae*] {Incyte PD:1923722}
52. *Homo sapiens* carbonic anhydrase precursor (CA 12) mRNA, complete cds {Incyte PD:3766382}
53. *H.sapiens* mRNA for SIX1 protein {Incyte PD:3208486}
54. Plasminogen activator inhibitor, type I {Incyte PD:1445767}
55. Human mRNA for SHPS-1, complete cds {Incyte PD:2180684}
56. Collagen, type V, alpha 1 {Incyte PD:1672442}
57. *Homo sapiens* monocarboxylate transporter (MCT3) mRNA, complete cds {Incyte PD:1343253}
58. Human follistatin gene {Incyte PD:1577614}
59. Human putative RNA binding protein (RBP56) mRNA, complete cds {Incyte PD:1907369}
60. *Homo sapiens* mRNA for PRP8 protein, complete cds {Incyte PD:3616229}
61. *Homo sapiens* CAGH3 mRNA, complete cds {Incyte PD:1432042}
62. EST {Incyte PD:2953888}
63. Intercellular adhesion molecule 1 (CD54), human rhinovirus receptor {Incyte PD:1556061}
64. Human p120E4F transcription factor mRNA, complete cds {Incyte PD:1940164}
65. Collagen, type VI, alpha 1 {Incyte PD:2672056}
66. Human mRNA for pM5 protein {Incyte PD:1578951}
67. ALZHEIMER'S DISEASE AMYLOID A4 PROTEIN PRECURSOR {Incyte PD:126370}
68. Human mRNA for KIAA0062 gene, partial cds {Incyte PD:3138128}
69. Human clone HSH1 HMG CoA synthase mRNA, partial cds {Incyte PD:1807407}
70. Filamin 1 (actin-binding protein-280) {Incyte PD:1708528}
71. Synteni: YCFR 85 {YC 85.2000.X}
72. Synteni: YCFR 46 Cy3 {YC 46.2000.W}
73. Homologue of mouse tumor rejection antigen gp96 {Incyte PD:2679349}
74. Tissue inhibitor of metalloproteinase 3 (Sorsby fundus dystrophy, pseudoinflammatory) {Incyte PD:418041}
75. Human XMP mRNA, complete cds {Incyte PD:1887661}
76. Cytochrome P450, subfamily XIA (cholesterol side chain cleavage) {Incyte PD:2368282}
77. Granulin {Incyte PD:812141}
78. Human extracellular matrix protein 1 (ECM1) mRNA, complete cds {Incyte PD:1965806}
79. 78 KD GLUCOSE REGULATED PROTEIN PRECURSOR {Incyte PD:2884613}
80. Synteni: YCFR 21 {YC 21.2000.X}
81. *Homo sapiens* mRNA for serin protease with IGF-binding motif, complete cds {Incyte PD:1958902}
82. Inhibitor of DNA binding 1, dominant negative helix-loop-helix protein {Incyte PD:1687060}
83. Solute carrier family 6 (neurotransmitter transporter, taurine), member 6 {Incyte PD:1516886}
84. Hormone receptor (growth factor-inducible nuclear protein N10) {Incyte PD:1958560}
85. Fibulin 2 {Incyte PD:1901095}
86. Kinase insert domain receptor (a type III receptor tyrosine kinase) {Incyte PD:2220338}
87. Synteni: YCFR 45 {YC 45.2000.X}
88. Syndecan 4 (amphiglycan, ryudocan) {Incyte PD:3214670}

TABLE 6-continued

Waveform Up Regulated Genes in Ascending Order (Lowest to Highest)

89. Synteni: YCFR 21 {YC 21.0500.N}
90. Human pre-B cell enhancing factor (PBEF) mRNA, complete cds {Incyte PD:1641590}
91. Cytochrome P450, subfamily IIC (mephenytoin 4-hydroxylase) {Incyte PD:168865}
92. Latent transforming growth factor beta binding protein 1 {Incyte PD:1313183}
93. Lysyl hydroxylase {Incyte PD:1759127}
94. Human mRNA for KIAA0230 gene, partial cds {Incyte PD: 1449824}
95. Human mRNA for dihydropyrimidinase related protein-2, complete cds {Incyte PD:2784546}
96. *H.sapiens* garp gene mRNA, complete CDS {Incyte PD:3572014}
97. EST {Incyte PD:724880}
98. ESTs, Weakly similar to TRANSMEMBRANE PROTEIN SEX PRECURSOR [*H.sapiens*] {Incyte PD:1511346}
99. Human contactin associated protein (Caspr) mRNA, complete cds {Incyte PD:2309047}
100. Human cysteine-rich fibroblast growth factor receptor (CFR-1) mRNA, complete cds {Incyte PD:2204871}
101. EST {Incyte PD:2580841}
102. Collagen, type V, alpha {Incyte PD:1887959}
103. *H.sapiens* RNA for type VI collagen alpha3 chain {Incyte PD:1314882}
104. Protein kinase C substrate 80K-H {Incyte PD:1723971}
105. Fibrillin 1 (Marfan syndrome) {Incyte PD:1448051}
106. Collagen, type XI, alpha 1 {Incyte PD:3598222}
107. *H.sapiens* mRNA for extracellular matrix protein collagen type XIV, C-terminus {Incyte PD:2208990}
108. Collagen, type II, alpha 1 (primary osteoarthritis, spondyloepiphyseal dysplasia, congenital) {Incyte PD:2518178}
109. ESTs, Weakly similar to unknown [*S.cerevisiae*] {Incyte PD:2171401}
110. EST {Incyte PD:1923572}
111. Human insulin-like growth factor binding protein 5 (IGFBP5) mRNA {Incyte PD:1686585}
112. Human mRNA for KIAA0242 gene, partial cds {Incyte PD:1940994}
113. Complement component 1, s subcomponent {Incyte PD:1904751}
114. Human chromosome 17 unknown product mRNA, complete cds {Incyte PD:2849603}
115. *Homo sapiens* lysosomal pepstatin insensitive protease (CLN2) mRNA, complete cds {Incyte PD:3500996}
116. Collagen, type IV, alpha 2 {Incyte PD:1906574}
117. ESTs, Moderately similar to ZINC FINGER PROTEIN HF.12 [*Homo sapiens*] {Incyte PD:3729155}
118. *Homo sapiens* stanniocalcin precursor (STC) mRNA, complete cds {Incyte PD:2222921}
119. P55-C-FOS PROTO-ONCOGENE PROTEIN {Incyte PD:341491}
120. EST {Incyte PD:2424631}
121. EST {Incyte PD:1940710}
122. Thrombospondin 1 {Incyte PD:2055534}
123. Complement component C1r {Incyte PD:1664320}
124. REGULATOR OF G-PROTEIN SIGNALLING 2 {Incyte PD: 1218114}
125. INTEGRAL MEMBRANE PROTEIN E16 {Incyte PD:1911012}
126. Collagen, type I, alpha 1 {Incyte PD:782235}
127. *H.sapiens* mRNA for adipophilin {Incyte PD:1985104}
128. EST {Incyte PD:1979450}
129. EST {Incyte PD:690994}
130. Cathepsin D (lysosomal aspartyl protease) {Incyte PD:3940755}
131. Matrix metalloproteinase 2 (gelatinase A, 72kD gelatinase, 72kD type IV collagenase) {Incyte PD:1558081}
132. Cyclin D2 {Incyte PD:1618422}
133. EST {Incyte PD:2636514}
134. COMPLEMENT C3 PRECURSOR {Incyte PD:1513989}
135. *Homo sapiens* secreted frizzled related protein mRNA, complete cds {Incyte PD:428236}
136. INSULIN-LIKE GROWTH FACTOR BINDING PROTEIN 3 PRECURSOR {Incyte PD:1447903}
137. Fibronectin 1 {Incyte PD:3553729}
138. Early growth response protein 1 {Incyte PD:1705208}
139. Human autoantigen DFS70 mRNA, partial cds {Incyte PD:42920}
140. Prostaglandin-endoperoxide synthase 2 (prostaglandin G/H synthase and cyclooxygenase) {Incyte PD:3139163}

TABLE 6-continued

Waveform Up Regulated Genes in Ascending Order (Lowest to Highest)

141. Synteni: YCFR 43 {YC 43.2000.W}
142. Synteni: YCFR 43 {YC 43.2000.Z}
143. Synteni: YCFR 23 {YC 23.0062.N}
144. Synteni: YCFR 43 {YC 43.2000.Y}
145. *Homo sapiens* phosphomevalonate kinase mRNA, complete cds {Incyte PD:1497123}
146. Synteni: YCFR 43 {YC 43.2000.X}
147. Synteni: YCFR 23 {YC 23.0031.N}
148. CARTILAGE GLYCOPROTEIN-39 PRECURSOR {Incyte PD:157510}
149. Synteni: YCFR 23 {YC 23.0125.N}
150. Synteni: YCFR 23 {YC 23.0250.N}
151. Synteni: YCFR 23 {YC 23.4000.N}
152. Human germline oligomeric matrix protein (COMP) mRNA, complete cds {Incyte PD:2636634}

EXAMPLE 7

Prototype of the System

Figure 10:
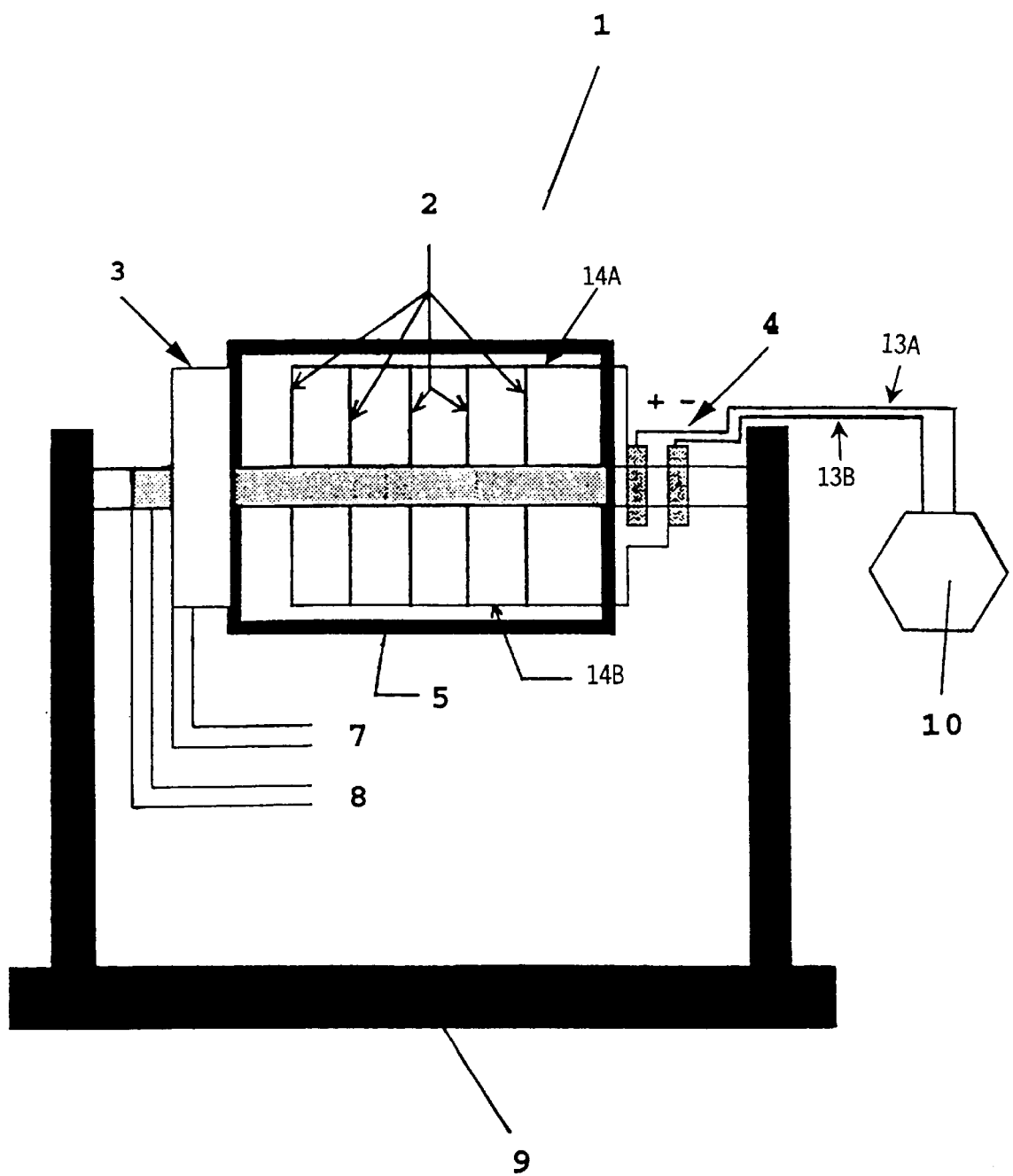
FIG. 10 shows prototype of the system 1, consisting of silicon plates 2, fluid coupling 3, slip rings 4, a rotating wall pressure vessel (RWPV) 5, electrical conductor 6 (i.e., an electrical conductive bioattractive inlay strip), a perfusion inlet 7, perfusion outlet 8, a stand for the rotating wall pressure vessel 9 and a source of time varying electrical current 10.

FIGS. 10 and 11 are partially diagrammatic representations of one embodiment of the system 1. Spherical disks 2 of biocompatable material are arranged along the horizontal spin filter or horizontal oxygenator of a standard rotating wall perfused vessel or rotating wail batch-fed vessel 5.

Figure 11B:
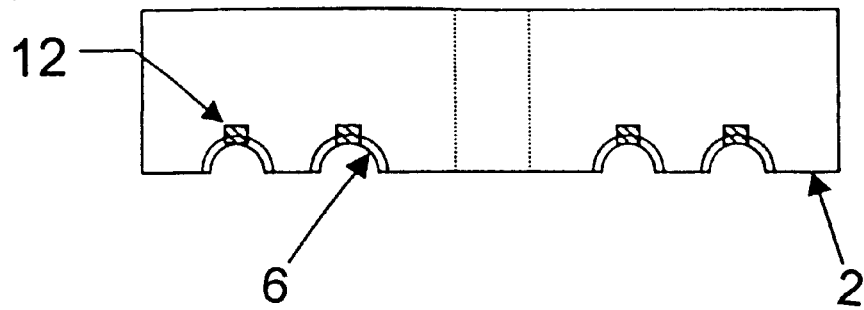
FIG. 11B is a side view of the silicon plate 2, demonstrating the electrical contacts 12 and the electrical conductive strips, in the form of bioattractive inlays 6.
Figure 11A:
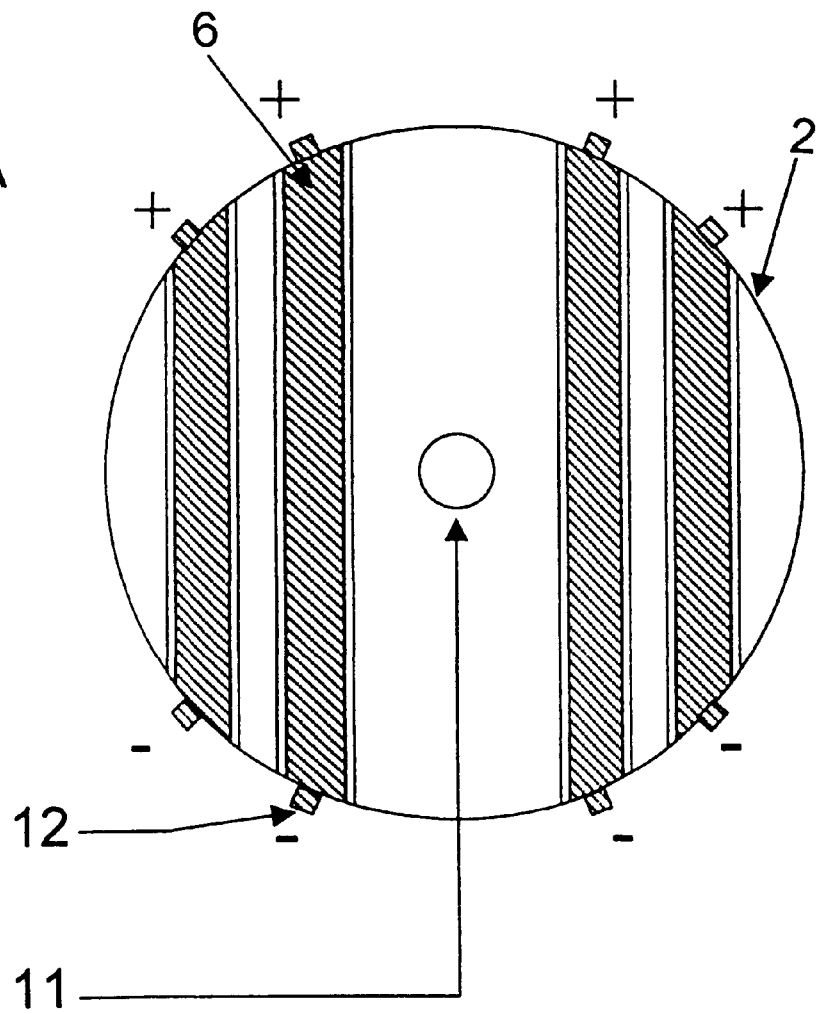
FIG. 11A is a plan view of one of the disc-shaped silicon plates 2, showing a central opening 11 about which rotation occurs, the electrical conductors 6, and electrical contacts 12 connected to the strips at opposite ends thereof.

The electrically conductive, bioattractive strips 6 are each suitably embedded in or affixed to each of the disks such that each disk has a positive and negative pole 12, associated with positive and negative terminals 12 connected to respective endportions of the strips, as shown in FIG. 11A. As will be more fully described, in one preferred embodiment in which an alternating current is applied to the strips, the polarity of the strips changes cyclically in correspondence with the change in polarity of the applied current. Each biocompatable disk is preferably two-sided, allowing growth of tissue on both the left and right portions of the spherical disk. Sterilization of the reactor core is effected by one of multiple sterilization procedure, either ethylene oxide sterilization, autoclave sterilization if the polymer permits, or in the case of the batch-fed vessel, sterilization with hydrogen peroxide. After sterilization and sufficient detoxification procedures, cellular material is seeded into the reactor at a level to be determined according to the cell line of interest.

A source of time varying current 10, suitably a laboratory current source with adjustable wave-form output connected to a remote power source, not shown, is operable to provide a time varying current, suitably of a value of about 1 mA to about 1,000 mA, in the present embodiment. The time varying current is suitably an alternating current, as indicated above, although in other embodiments it is a pulsating DC current. The current is conducted from the source 10 along first and second conductors 13A and 13B to slip rings 4. The slip rings are non-rotatable relative to the vessel 5, and therefore rotate with the vessel during operation. Current received through conductors 13A and 13B is conducted through the associated slip rings to first and second sets of conductors, represented by first and second conductors 14A and 14B, which are preferably insulated with an insulative material, not shown, compatible with the fluids and products within the bioreactor chamber. Each conductor is mechanically connected to a respective peripheral portion of each of the respective discs, and electrically connected with an end portion of one of the conductive strips 6 (FIGS. 11A and 11B). As viewed in FIG. 10, conductor 14A and the associated slip ring are indicated to be of positive (+) polarity, and conductor 14B and its associated slip ring are indicated to be of relatively negative (−) polarity. As suggested above, upon the current changing in polarity, conductor 14A will momentarily have a negative potential relative to conductor 14B, thereby permitting a time varying current, which in this embodiment is an alternating current, to flow through conductor 6 which. In other embodiments, the time-varying current may be in the form of a pulsating DC current, suitably a square wave or other waveform, rather than an alternating current, in which case the conductors 14A and 14B and their associated slip rings remain of the same polarity but of differing potentials.

After inoculation, the rotating wall vessel 5 is rotated at an appropriate speed and single cellular material begins to attach onto the surface of the biocompatable material 6. After initial growth of one 24- or 48-hour period, electrical stimulation, i.e., potentiation, begins via continuous low-level or pulsatile electrical flow through each disk in series.

Discussion

Use of the methods of the present invention to control the proliferative rate of normal human adult astrocytes and normal human neural progenitor cells (NHNP) has been demonstrated. The procedure is applicable to, but not limited to, the control of normal human neural cells in both two-dimensional and three-dimensional culture. As presented in the molecular genetic data shown in Table 5 and Table 6, many of the genetic responses in both up regulated and down regulated genes are maturation and growth regulatory in nature. An inspection reveals these genes are also primarily involved in the embryogenic process. Therefore it is reasonable to conclude that control over the embryogenic development process can be achieved via the presently demonstrated methodology.

As shown in Table 6, specific genes such as human germline oligomeric matrix protein, prostaglandin endoperoxide synthase 2, early growth response protein 1, and insulin like growth factor binding protein 3 precursor are highly up regulated, while Keratin Type II cytoskelatal 7, mytotic kinesin like protein 1, transcription factor 6 like 1, mytotic feedback control protein, and cellular retinoic acid binding protein are down regulated (Table 5). Each of these two sets or classes of genes are only examples from the sum of approximately 320 genes changes expressed as a consequence of exposure to electrical potentiation.

As is clearly demonstrated in the human body, the bioelectric, biochemical process of electrical nerve stimulation is a documented reality. The present invention demonstrates that the same phenomena can be potentiated in a synthetic atmosphere, i.e., in rotating wall cell culture vessels. As may be understood from the forgoing discussion, this electrical potentiation can be used for a number of purposes.

The following references were cited herein.
1. Schwarz et al., U.S. Pat. No. 4,988,623, (1991).
2. Schwarz et al., U.S. Pat. No. 5,026,650, (1991).
3. Goodwin, et al., *In Vitro Cell Dev. Biol.,* 28A: 47–60 (1992).
4. Goodwin, et al., *Proc. Soc. Exp. Biol. Med.,* 202: 181–192 (1993).
5. Goodwin, et al., *J. Cell Biochem.,* 51: 301–311 (1993).
6. Goodwin, et al., *In Vitro Cell Dev. Biol. Anim.,* 33: 366–374 (1997).
7. Fukuda et al., U.S. Pat. No. 5,328,843
8. Aebischer, U.S. Pat. No. 5,030,225

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A system for growing biological cells, comprising:
    a rotating cell culture vessel;
    a cell culture medium contained within said rotating cell culture vessel;
    an electrode; and
    an electrical circuit connected to said electrode for passing a time varying electrical current through said electrode for generating a time varying electromagnetic field within said cell culture medium.

2. The system of claim 1, wherein said time varying electrical current is in the form of an alternating current.

3. The system of claim 1, wherein said time varying electrical current is in the form of a square wave.

4. The system of claim 1, wherein said electrode is adjacent to and spaced from said rotational cell culture vessel.

5. The system of claim 1, wherein said electrode is positioned within said rotational cell culture vessel.

6. The system of claim 1, wherein said electrical current is from about 1 mA to about 1,000 mA.

7. The system of claim 6, wherein said time varying electrical current is about 1 milliamperes to about 6 milliamperes.

8. The system of claim 1, wherein said time varying electromagnetic field induces a cellular response at gene level.

9. The system of claim 8, wherein said cellular response is cellular control of growth and differentiation at gene level.

10. The system of claim 9, wherein said cellular control of growth and differentiation is to suppress or enhance growth regulatory functions at gene level.

11. The system of claim 10, wherein said gene is associated with embryogenesis.

12. The system of claim 1, wherein said electrode is made of a material selected from the group consisting of titanium, zirconium, platinum and stainless steel.

13. The system of claim 1, wherein said electrode comprises an antenna for emitting said time varying electromagnetic field within said cell culture medium.

14. The system of claim 13, wherein said antenna is positioned adjacent said rotating cell culture vessel, said antenna comprising means for inducing an electromagnetic field within said medium within said rotating cell culture vessel.

15. The system for growing biological cells of claim 1, wherein the frequency of said time varying electrical current is approximately 10 Herz.

16. A system for growing biological cells in a two-dimensional array, wherein said cells exhibit accelerated growth, comprising:

a cell culture medium;

a container;

an electrode positioned within said container;

said biological cells, wherein said biological cells contained in said cell culture medium are bubbled onto said electrode; and an electrical circuit connected to said electrode for passing a time varying electrical current through said electrode for generating a time varying electromagnetic field within said cell culture medium.

17. The system of claim 16, wherein said electrode is positioned adjacent said container.

18. The system of claim 16, wherein said electrode is positioned within said container.

19. The system of claim 16, wherein said biological cells comprise neural cells.

20. The system of claim 16, further comprising:

a slide placed on said electrode wherein said biological cells contained in said cell culture medium are bubbled thereon.

21. The system of claim 16, wherein said time varying electrical current is in the form of an alternating current.

22. The system of claim 16, wherein said time varying electrical current is in the form of a square wave.

23. The system of claim 16, wherein said electrical current is from about 1 millamperes to about 1,000 1 millamperes.

24. The system of claim 16, wherein said electrical current is from about 1 millamperes to about 6 millamperes.

25. The system of claim 16, wherein said electrical is made of a material selected from the group consisting of titanium, zirconium, platinum and stainless steel.

* * * * *